(12) United States Patent
Rijken et al.

(10) Patent No.: US 9,751,360 B2
(45) Date of Patent: Sep. 5, 2017

(54) BIDIRECTIONAL MOVEMENT ASSEMBLY

(75) Inventors: Antonius Maria Rijken, Eindhoven (NL); Martinus Antonius Maria Cuppen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1082 days.

(21) Appl. No.: 13/386,548

(22) PCT Filed: Sep. 1, 2010

(86) PCT No.: PCT/IB2010/053922
§ 371 (c)(1),
(2), (4) Date: Jan. 23, 2012

(87) PCT Pub. No.: WO2011/030255
PCT Pub. Date: Mar. 17, 2011

(65) Prior Publication Data
US 2012/0155616 A1 Jun. 21, 2012

(30) Foreign Application Priority Data
Sep. 8, 2009 (EP) .................................... 09169724

(51) Int. Cl.
*A61B 6/00* (2006.01)
*B60B 19/00* (2006.01)
(52) U.S. Cl.
CPC .......... *B60B 19/003* (2013.01); *A61B 6/4405* (2013.01); *B60B 2200/26* (2013.01); *B60B 2900/531* (2013.01)
(58) Field of Classification Search
CPC ...... F16H 3/003; A61B 6/4405; B60B 19/003
See application file for complete search history.

(56) References Cited

U.S. PATENT DOCUMENTS 3,789,699 A * 2/1974 Guichard ..................... 475/186
3,789,947 A * 2/1974 Blumrich ..................... 180/6.48
(Continued)

FOREIGN PATENT DOCUMENTS

DE 822660 C 11/1951
EP 0768076 A1 4/1997
(Continued)

OTHER PUBLICATIONS

Smith (WO 86/03132). Jun. 5, 1986.*
Cojocaru, "Evolution of Multidirectional Wheels Researches", Analele Universitatii, Anul XIII, NR, 1, 2006, pp. 127-132.

*Primary Examiner* — David J Makiya
*Assistant Examiner* — Dani Fox

(57) ABSTRACT

The present invention relates to motor assisted movement as well as to mobile X-ray systems comprising at least one bidirectional wheel. Positioning heavy objects in in particular confined spaces with high precision may be a cumbersome and tedious task. Consequently, a motor assisted movement assembly as well as an X-ray system comprising at least one bidirectional wheel is presented. According to the present invention a motor assisted movement assembly (19) comprising at least one bidirectional wheel (18) and a motor arrangement associated with the at least one bidirectional wheel (18) is provided. The motor assisted movement assembly (19) is adapted to move on a surface, wherein the at least one bidirectional wheel (18) is adapted to roll in at least a first direction (20) and in at least a second direction (22), with the first direction (20) and the second direction (22) being non-parallel. The motor assisted movement assembly (19) is adapted to detect an indication of a desired movement (16) of the motor assisted movement assembly (19) relative to the surface and the motor arrangement is adapted to assist the movement of the motor assisted move- (Continued)

ment assembly (19) relative to the surface in accordance with the indication (16).

35 Claims, 7 Drawing Sheets

(56) References Cited

U.S. PATENT DOCUMENTS

| | | | |
|---|---|---|---|
| 6,131,690 A * | 10/2000 | Galando et al. | 180/411 |
| 6,302,226 B1 * | 10/2001 | Kanno et al. | 180/6.5 |
| 6,409,382 B1 * | 6/2002 | Akutsu et al. | 378/198 |
| 7,056,185 B1 * | 6/2006 | Anagnostou | 446/456 |
| 2004/0010851 A1 * | 1/2004 | Nagaoka et al. | 5/618 |
| 2004/0167397 A1 | 8/2004 | Brill et al. | |
| 2005/0134106 A1 | 6/2005 | Guile | |
| 2010/0117754 A1 | 5/2010 | Yamamoto | |

FOREIGN PATENT DOCUMENTS

| | | |
|---|---|---|
| EP | 1346666 A1 | 9/2003 |
| JP | 2002067962 A | 3/2002 |
| JP | 2006141669 A | 6/2006 |
| WO | 8603132 A1 | 6/1986 |
| WO | 2006062905 A2 | 6/2006 |
| WO | 2007075699 A2 | 7/2007 |

* cited by examiner

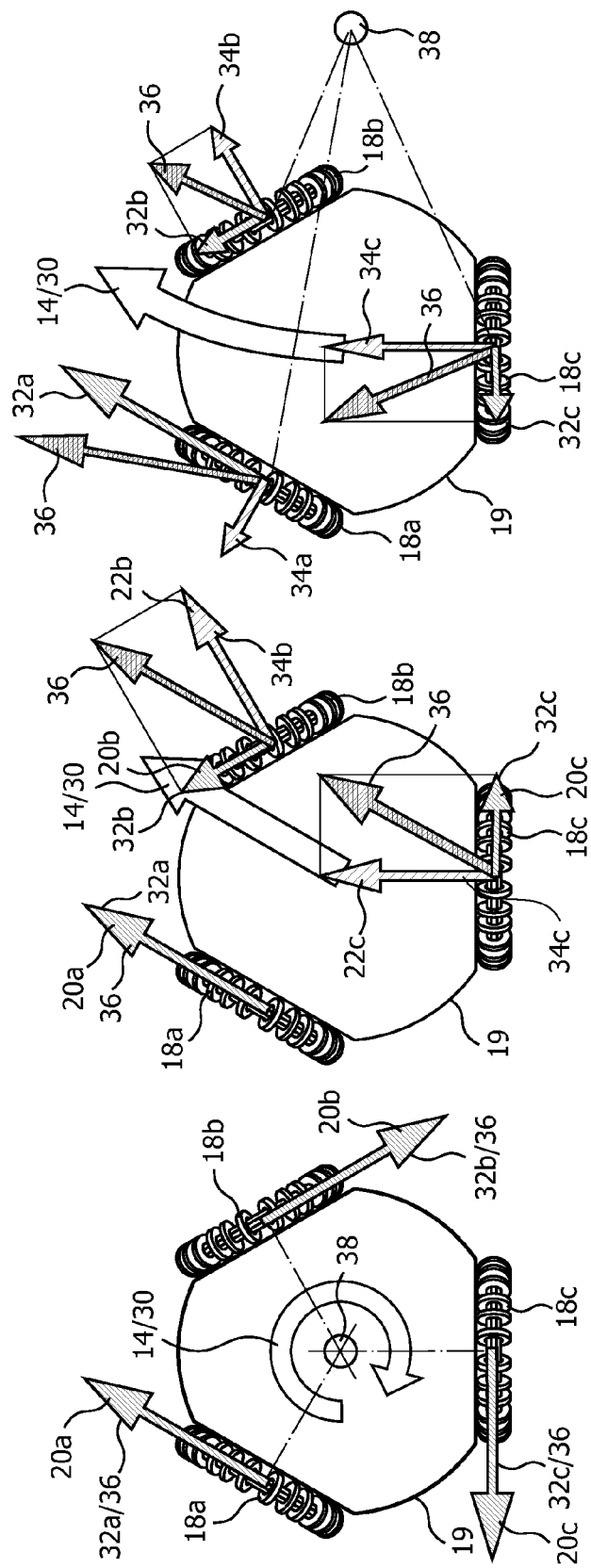

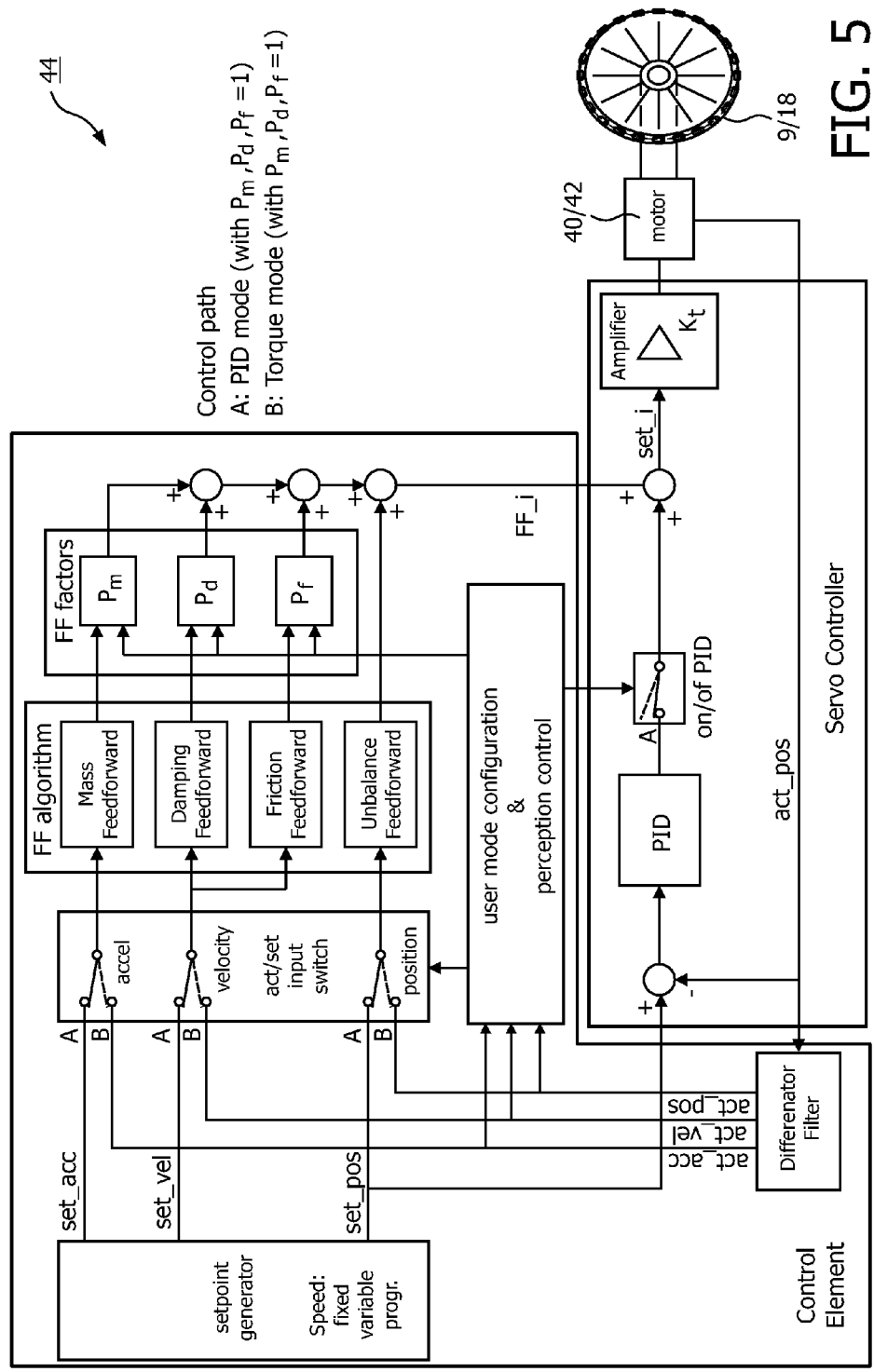

BIDIRECTIONAL MOVEMENT ASSEMBLY

TECHNICAL FIELD OF THE INVENTION

The present invention relates to bidirectional movement of a moving assembly in general and in particular in a medical application. More particular, it relates to motor assisted movement assembly comprising a bidirectional wheel as well as an X-ray system comprising a bidirectional wheel.

In particular, it relates to movement and the positioning of an X-ray system relative to an object to be examined.

BACKGROUND OF THE INVENTION

X-ray systems are in particular used for diagnostic purposes e.g. for acquiring X-ray images of an object to be examined.

For acquiring X-ray images, an X-ray system regularly comprises an X-ray generating device and an X-ray detector. The X-ray generating device and the X-ray detectors are arranged on opposite sides of the object to be examined and are operatively coupled for the acquisition of X-ray images. X-radiation is emitted by the X-ray generating device towards the X-ray detector. An object to be examined situated between the X-ray detector and the X-ray generating device is thus penetrated by X-radiation. Detector elements of the X-ray detector acquire information in accordance with spatially attenuated X-radiation, which information is subsequently used for the generation of an X-ray image of the object.

Regularly, both the X-ray generating device and the X-ray detector are heavy, rigidly built elements having a substantial weight. Thus, for moving an X-ray system on a surface, e.g. on the floor of an operating room, a substantial force has to be applied to the X-ray system for a desired placement and positioning.

In particular, precise positioning with regard to the object to be examined, thus positioning within precise tolerances, may be required.

SUMMARY OF THE INVENTION

Thus, there may be a need for an assisted, however controlled movement and positioning of a device, in particular an X-ray system, relative to an object, e.g. to be examined, with reduced force requirements and increased handling and positioning accuracy.

In the following, a motor assisted movement assembly, an X-ray system, a method of motor assisted movement as well as the use of a motor assisted movement assembly according to the independent claims are provided.

According to an exemplary embodiment of the present invention, a motor assisted movement assembly is provided, comprising at least one bidirectional wheel and a motor arrangement associated with the at least one bidirectional wheel. The motor assisted movement assembly is adapted to move on a surface and is adapted to detect an indication of a desired movement of the motor assisted movement assembly relative to the surface. The at least one bidirectional wheel is adapted to roll in at least a first direction and in at least a second direction, with the first direction and the second direction being non-parallel. The motor arrangement is adapted to assist the movement of the motor assisted movement assembly relative to the surface in accordance with the indication.

According to a further exemplary embodiment of the present invention, an X-ray system is provided, comprising an X-ray generating device, an X-ray detector and at least one bidirectional wheel. The at least one bidirectional wheel is adapted for moving the X-ray system on a surface and is adapted to roll in at least a first direction and in at least a second direction, with the first direction and the second direction being non-parallel. The X-ray generating device and the X-ray detector are operatively coupled for the acquisition of X-ray images of an object to be examined.

According to a further exemplary embodiment of the present invention, a method for motor assisted movement is provided, comprising the steps of applying an external force to the motor assisted movement assembly as a manual indication of a desired movement of a motor assisted movement assembly relative to a surface detecting the external force in a motor assembly or a motor element and assisting the desired movement.

According to a further exemplary embodiment of the present invention, a motor assisted movement assembly according to the present invention is used in at least one of an X-ray system, a mobile X-ray system and a C-arc system.

For example, in an intraoperative scenario, a mobile X-ray system may be employed, e.g. a C-arc X-ray system. An operator, e.g. an X-ray technician, may be required to acquire relevant images for e.g. a surgeon before, during and after an operation. Space requirements or space limitations within an OR, in particular during an operation, may require the positioning of the mobile X-ray system afar from the operating table during a time no image is to be acquired. Consequently, when the necessity arises for the acquisition of X-ray images, the mobile X-ray system may have to be moved in and out of the operating field for acquiring X-ray images and subsequent storage of the X-ray system. Since a mobile X-ray system, in particular due to the substantial weight of both the X-ray generating device and the X-ray detector, may itself constitute a heavy piece of equipment, the relocation of the X-ray system may be a tedious duty.

Thus, a motor assisted however manually controlled movement of an X-ray system for moving on a surface may be beneficial.

The operator may initiate a desired movement, e.g. moving a mobile X-ray system towards the operating table. The X-ray system or at least parts of it may detect the initiated movement or at least an indication of a desired movement, like for example a force provided to the mobile X-ray system for determining a desired movement, e.g. a spatial vector in the direction of the desired movement.

The mobile X-ray system, in particular a control element adapted to detect the desired movement and its movement vector respectively may engage a suitably arranged motor element which may add an overlaying or additional force. An according supporting force by the at least one motor element may decrease the feeling of friction and/or mass perceived by an operator desiring to move the mobile X-ray system. In other words, an operator may provide a manual indication to the X-ray system, e.g. moving or pushing the X-ray system in the desired direction. The mobile X-ray system may detect the desired direction and may engage at least one motor element to support the movement in the desired direction.

When using a, in particular manual, indication of a desired movement, e.g. by pushing the X-ray system, sensors, switches or the like may not be required for steering or controlling the X-ray system and its direction of movement respectively. Thus, a separate, dedicated "move enable" actuator, switch or button may not be required. However, an according actuator, switch or button may be beneficial for a fully automated moving mode. E.g., a joystick may be employed for indicating the direction, thus a vector of a desired movement of the X-ray system on the surface.

Further functions may be implemented like programmable arret stops for the guidance to preferred or preset positions, e.g. for relocating the X-ray system to a defined and/or previously used position. Also the implementation of individual user profiles with different, individual levels of motor assistance are conceivable.

The motor element may in particular be implemented with having a direct drive behaviour, e.g. by using a direct drive motor element. A direct drive motor element may be seen as a motor element that does not require or employ a separate gearbox having a gear transmission ratio.

In particular, the use of a direct drive motor element may allow different modes of operation, e.g. a drive operation mode, a clutch operation mode or freewheeling operation mode and a break operation mode.

The drive operation mode may allow for a manually controlled motor assisted movement.

A further drive mode, e.g. an automated drive mode or motorized drive mode may be implemented by employing user interface elements like e.g. buttons, switches, a joystick or even speech control. A further mode of operation may be the clutch operation mode or the freewheeling operation mode. An according mode may be achievable by interrupting power supplied to the motor element. Here, a substantially free running motor element may be obtained which may be considered to be essentially free running without requiring further applied forces over a non-motor-assisted manual movement of the X-ray system.

Furthermore, a break operation mode is conceivable, in which the X-ray system may stop at a predefined position and may even be kept in said position by the motor element counteracting, possibly unintentionally, applied forces to the X-ray system, e.g. by the person bumping into the X-ray system unintentionally.

Motor elements may be of a brushed or brushless nature. A brushless motor element may in particular provide good control behaviour at high torques and low speeds including zero speed. Consequently, low gearing drive trains or direct drive elements may be employed which results in a highly efficient transmission of forces.

Furthermore, by employing the direct drive principle, e.g. a direct drive motor element, the motor element current may be a preferred measure or indication for a respective torque at a defined load, e.g. due to an applied torque or force to the X-ray system. A motion control element may be set to torque or current mode, where an applied torque or force to the motor element may be determined by a resulting motor current or differential motor current, which may be the basis for the motor assist functionality. In other words, the motor may determine the direction in which an operator is pushing or pulling the X-ray system, in which case a motor element is activated to assist the movement in that desired direction, e.g. by powering the motor element to move the X-ray system in the desired direction.

Further functions like arret stops, preferred positioning and breaking may be implemented by substantially instantaneous switching, e.g. "on the fly switching", from a torque mode to a speed or position mode. In the speed or position mode, it may be preferable to determine an absolute or at least a relative position of the X-ray system versus the surface on which it is to be moved.

A further issue of the motor assist functionality may be the safety aspect. Regularly, when employing motor elements in the vicinity of an object to be examined, e.g. a patient, an according motorized system may be controlled under "dead man control". Here, by employing a dedicated button or switch, which is to be released in case of a failure or operation error the motor element is deactivated, thus the movement is stopped substantially immediately.

Since an aspect of the present invention may be seen as the emission of a dedicated actuating element, e.g. a switch or button for the control and/or initiation of a motor driven movement, further safety measures may have to be implemented. Accordingly, e.g. the torque and/or movement speed of an assisted movement may be limited to a level which requires a substantially constant force or indication of a desired movement from an operator. In this case, if the constant force or indication is not present any more, the movement may also be stopped essentially immediately. An according safety feature may meet the "single fault safety requirement", meaning that any single component failure or failure to provide the required constant force or indication may lead to the substantial immediate shutdown of the motor assisted movement in/to a safe state, subsequently preventing automatic operation until the respective problem has been corrected.

A further aspect of the present invention may be seen as the implementation of bidirectional wheels. By using bidirectional wheels with a mobile X-ray system, possibly combining bidirectional wheels with motor elements and/or a suitable control system, the mobile X-ray system may be moved in any direction or may rotate about any point.

A desired movement may be steered by a manual indication or by a control element and a user interface. With regard to the manual indication, the X-ray system may also be adapted to activate the motor elements such that it assists the operator while moving or positioning the X-ray system.

Unlike castor wheels regularly employed in X-ray systems, bidirectional wheels may in particular not need to turn in the direction of movement before actual movement occurs or even may be possible. Bidirectional wheels may start rolling in any direction substantially instantly when starting the desired movement. Bidirectional wheels may thus lead lower forces for initiating and sustaining a movement and may thus be capable of fine adjustment of the X-ray system with regard to an object without the need for employing small wigwag movements or small longitudinal movements, possibly in combination, for the precise positioning of an X-ray system.

In X-ray systems employing castor wheels, additional small movement axes may be designed in to provide a fine adjustment of the placement of the X-ray system. These small additional movement axes may be referred to as an axis for a wigwag movement, a small angular movement, and an axis for a small longitudinal movement, i.e. a small horizontal movement in the plane of movement of the X-ray system on a surface.

Employing bidirectional wheels may eliminate the requirement to implement such small movement axis. Bidirectional wheels may be seen as wheels that comprise two directions of movement, which are distinct from one another. In each direction of movement, the wheel may be adapted to be rolled substantially without any slippage.

A bidirectional wheel is regularly not turned to be movable or rollable in each of the two different directions. Thus, bidirectional wheels may allow a two-dimensional movement without requiring a steering gear or steering mechanism. In particular, a bidirectional wheel may comprise at least a first rolling element and at least a second rolling element, which are distinct from one another and both of which rolling elements are adapted for rolling in a specific direction, with those two directions being distinct from one another.

While the orientation of the two axes to one another may be arbitrary, it may be in particular beneficial in case the two directions, thus directions of movement, are substantially perpendicular to one another. Each of the at least two rolling elements, the first rolling element and the second rolling element may be combined with a suitable drive motor element to allow for a supported, assisted or even automatic movement or rolling of the first rolling element and the second rolling element in the first direction and the second direction respectively.

By combining a movement of the first rolling element and the second rolling element, an arbitrary movement in a two-dimensional plane may be obtainable. The resulting direction of movement may be determined by vector addition. The motor elements associated to the at least one first rolling element and the at least one second rolling element may be adapted to assist an operator in providing forces to the drive elements when the operator is positioning the X-ray system, e.g. with respect to a patient, by hand or manual indication, so that moving and positioning of a possibly heavy X-ray system may be performed easily and accurately.

In a motorized mode, motor elements may be actuated by a control element in accordance with a desired direction of movement, e.g. by employing a joystick for steering the X-ray system.

Thus, required forces needed for fine positioning an X-ray system may be reduced. A manual positioning may be performed accurately and conveniently by employing the motor assist mode while longitudinal and wigwag movements of additional small movement axes may be eliminated by employing bidirectional wheels.

In the following, further exemplary embodiments of the present invention are described relating in particular to a motor assisted movement assembly. However, it is to be understood that these explanations also apply to the X-ray system, to the method of motor assisted movement and to the use of a motor assisted movement assembly.

It is explicitly noted, that arbitrary variations and interchanges of single or multiple features between claimed entities, in particular between embodiments relating to apparatus type claims, method type claims and use type claims, are conceivable and within the scope and disclosure of the present patent application.

According to a further exemplary embodiment of the present invention, the at least one bidirectional wheel may comprise at least one first rolling element and/or at least one second rolling element, wherein the at least one first rolling element is adapted for rolling in the first direction and/or wherein the at least one second rolling element is adapted for rolling in the second direction.

By implementing a bidirectional wheel with individual rolling elements, which are adapted for rolling in different, distinct directions, the bidirectionality in movement may be easily implementable thus resulting in an arbitrary two-dimensional movement within a given plane, e.g. on the surface of a floor.

According to a further exemplary embodiment of the present invention, the motor arrangement may comprise at least one first motor element associated with the at least one bidirectional wheel, in particular with the at least one first rolling element, wherein the at least one first rolling element may be adapted to move the motor assisted movement assembly/first rolling element in the first direction.

By employing a motor element, an assisted or automated movement in the first direction may be easily obtainable.

According to a further exemplary embodiment of the present invention, the motor arrangement may further comprise at least one second motor element associated with the at least one bidirectional wheel, in particular with the at least one second rolling element wherein the at least one second motor element may be adapted to move the motor assisted movement assembly in the second direction.

With an according assisted or motorized movement in a second direction, the motor assisted movement assembly may be movable in a two-dimensional plane with reduced handling forces and increased positioning accuracy.

According to a further exemplary embodiment of the present invention, the motor arrangement, the first motor element and/or the second motor element may be adapted to detect the indication of a desired movement, a force and/or a torque acting on the motor arrangement, the first motor element and/or the second motor element.

An according indication, force or torque may be considered to be indicative for a desired movement direction. Thus, the motor arrangement, the first motor element and/or the second motor element may on the one hand be able to determine the direction of the desired movement while on the other hand may be able to directly support or assist the desired movement.

According to a further exemplary embodiment of the present invention, the indication may be a manual indication.

This may in particular be a force exerted on the motor assisted movement assembly without requiring dedicated buttons or switches or other control elements.

According to a further exemplary embodiment of the present invention, the motor assisted movement assembly may comprise at least one mode out of the group consisting of a drive mode, a clutch mode, a freewheeling mode, a break mode, a motor assist mode, a position mode and a motorized mode.

According modes or operation modes may allow to adapt the behaviour of the motor assisted movement assembly in general and the motor elements in particular to different operating scenarios, e.g. a drive mode, possibly in connection with a position mode, may allow an assisted positioning with increased accuracy of the motor assisted movement assembly, while a break mode, activated when a desired position has been acquired, may allow to precisely keep the motor assisted movement assembly at the desired position.

According to a further exemplary embodiment of the present invention, the motor assisted movement assembly may be adapted for automatically re-positioning.

Automatic re-positioning may allow the motor assisted movement assembly to be at least partially re-positioned automatically in/at a previously set or known position, e.g. by a control element or a control system, while taking into account relative movement with regard to the surface or even absolute positioning of the X-ray system, e.g. in a room.

According to a further exemplary embodiment of the present invention, the motor arrangement may be adapted to assist the movement of the motor assisted movement assembly by at least partly decreasing perceived moving resistance and/or moving force of the motor assisted movement assembly.

Thus, when assisting a desired movement, an operator may perceive a decreased moving resistance or moving force when trying to move or displace the motor assisted movement assembly due to motor elements being actuated in the desired direction of movement.

According to a further exemplary embodiment of the present invention, a motion control element may be provided for controlling the movement of the motor assisted movement assembly relative to the surface.

An according motion control element may be adapted to provide an indication or to accept an indication of a desired movement, possibly transforming it into an electric representation or a vector of desired movement, or controlling at least one of the first motor element and/or the second motor element for providing an assisted movement or even an automated movement.

According to a further exemplary embodiment of the present invention, the motor arrangement may be a direct drive motor arrangement.

A direct drive motor arrangement may in particular provide adequate feedback for determining a desired direction of movement.

In the following, further exemplary embodiments of the present invention are desired relating in particular to an X-ray system. However, it is to be understood that these explanations also apply to a motor assisted movement assembly, to the method of motor assisted movement and to the use of a motor assisted movement assembly.

According to a further exemplary embodiment of the present invention, the X-ray system may further comprise a motor assisted movement assembly according to the present invention, wherein the at least one bidirectional wheel is of the movement assembly.

In other words, the X-ray system comprising a motor assisted movement assembly altogether may still only comprise one bidirectional wheel. Providing a motor assisted movement assembly to the X-ray system may allow to easily and conveniently move and position an X-ray system with regard to a patient, e.g. an operation scenario.

These and other aspects of the present invention will become apparent from and elucidated with reference to the embodiments described hereinafter.

Exemplary embodiments of the present invention will be described below with reference to the following drawings.

The illustration in the drawings is schematic. In different drawings, similar or identical elements are provided with similar or identical reference numerals.

The figures are not drawn to scale, however may depict qualitative proportions.

BRIEF DESCRIPTION OF THE DRAWINGS

The figures show:
FIG. 4a-d different moving scenarios of motor assisted movement assemblies comprising bidirectional wheels according to the present invention;
FIG. 5 a schematic of an exemplary embodiment of a motion control system for a motor assisted movement assembly according to the present invention.

DETAILED DESCRIPTION OF EXEMPLARY EMBODIMENTS

Figure 1:
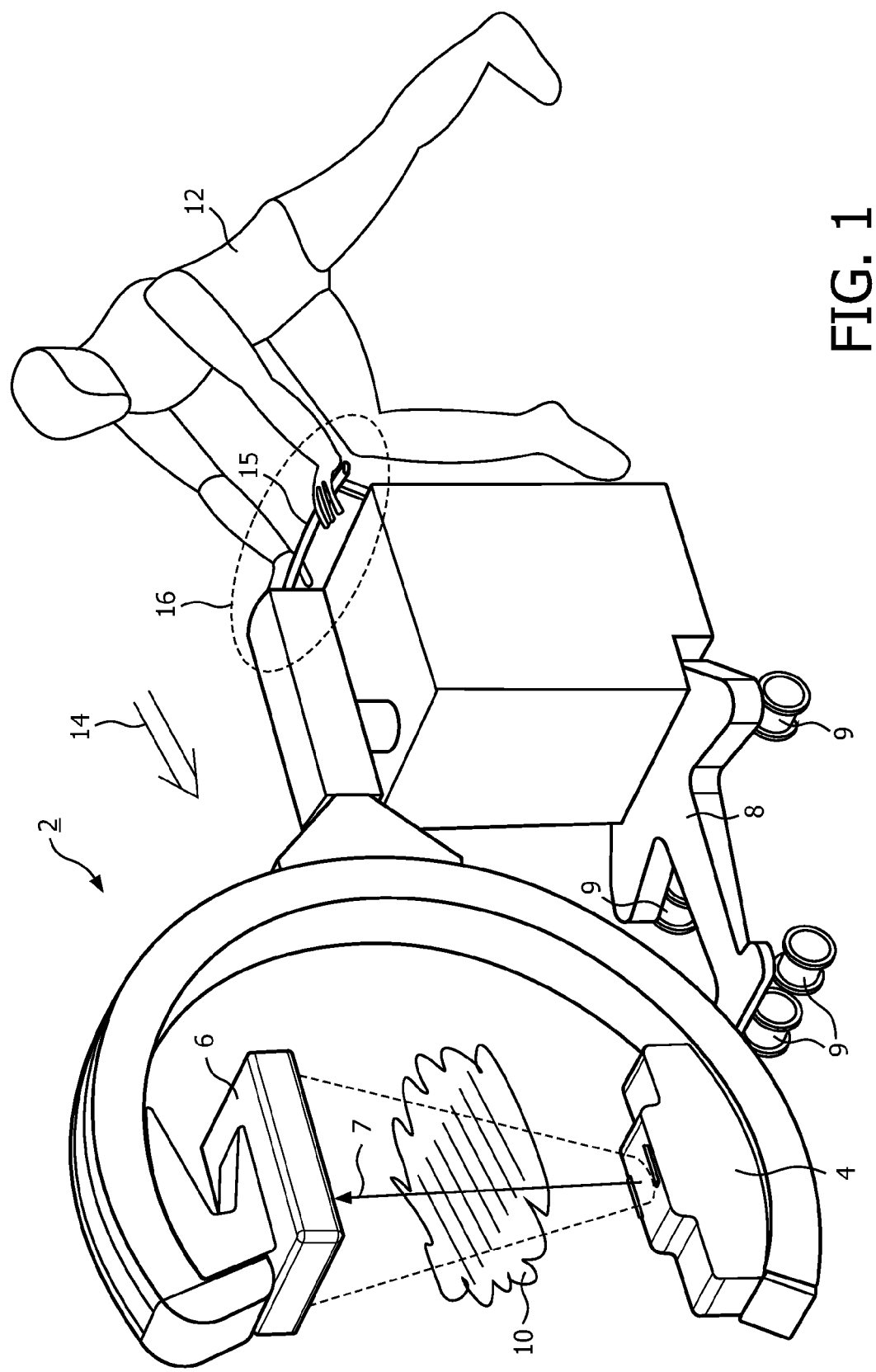
FIG. 1 an exemplary embodiment of moving an X-ray system.

Now referring to FIG. 1, an exemplary embodiment of moving an X-ray system is depicted.

In FIG. 1, an X-ray system 2, depicted exemplary as a C-arc system, comprises an X-ray generating device 4, e.g. an X-ray tube, and an X-ray detector 6. An object 10 is depicted schematically in the path of X-radiation 7 emanating from the X-ray generator 4 towards the X-ray detector 6, penetrating the object 10. A wheel arrangement 8 comprising wheels 9 is situated at the body of the X-ray system 2 for moving the X-ray system on a surface, e.g. the floor of an operating room.

An operator 12 is moving the X-ray system 2 in the direction of desired movement 14 by pushing the X-ray system 2 using a handle 15.

Thus, the operator 12 is applying an indication of desired movement 16 to the X-ray system 2 for moving the X-ray system 2 in the desired direction of movement 14.

Figure 2:
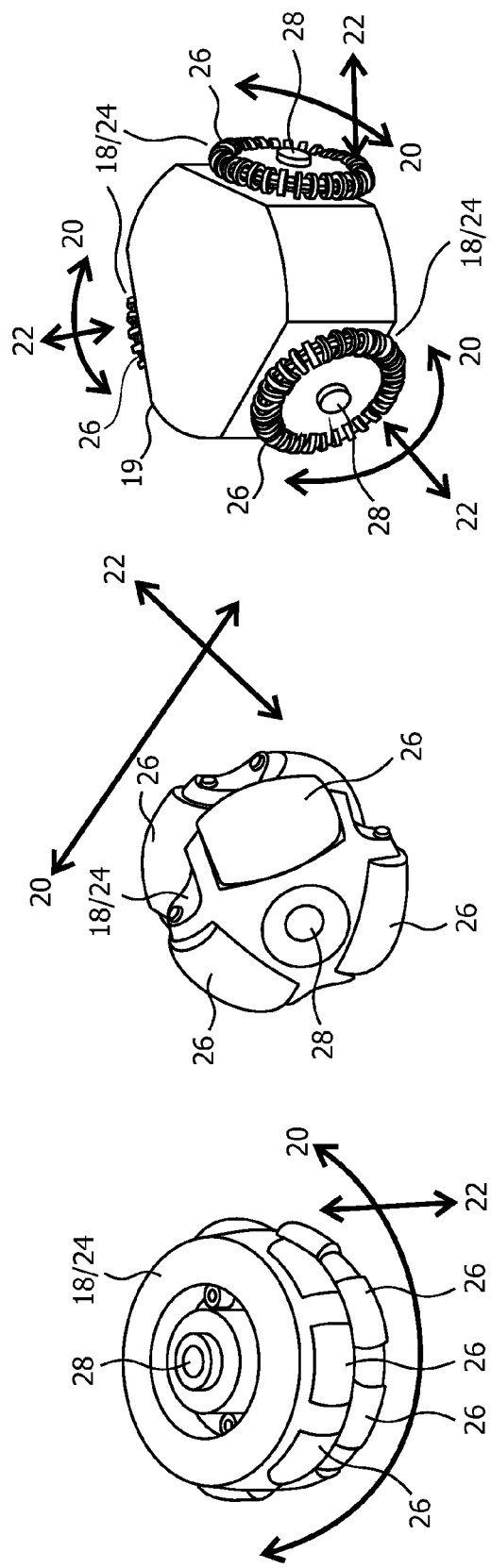
FIG. 2a-c exemplary embodiments of bidirectional wheels according to the present invention.

Now referring to FIGS. 2a-c, exemplary embodiments of bidirectional wheels according to the present invention are depicted.

FIGS. 2a,b in particular show individual embodiments of bidirectional wheels 18, while FIG. 2c shows an exemplary embodiment of a motor assisted movement assembly 19 comprising, here exemplaryly three bidirectional wheels 18.

In FIG. 2a, the bidirectional wheel 18 comprises an axis 28 for rotating the bidirectional wheel 18 in a first direction 20, substantially rolling on the circumference of the bidirectional wheel 18. The outer circumference of the bidirectional wheel 18 may thus be considered to be the first rolling element 24. Thus, the bidirectional wheel 18 may be rollable in a first direction 20 with or without dedicated first rolling elements 24 while comprising additional second rolling elements 26 for rolling in a second direction 22.

The second rolling elements 26 comprises two rows of individual rollers, which two rows are offset against one another to effectively bridge thew gap between two adjacent rolling elements 26 of one row by a rolling element 26 of the other row. Thus, no dead spot occurs in which the bidirectional wheel 18 may not be movable in the second direction 22. Again, the outer circumference of the bidirectional wheel 18 with regard to axis 28 or all second rolling elements 26 together may be considered as the first rolling element 24.

Now referring to FIG. 2b, a further embodiment of a bidirectional wheel 18 is depicted. In FIG. 2b, the individual second rolling elements 26 are substantially larger compared to the embodiment of FIG. 2a, while the basic principle is maintained.

Each row of individual second rolling elements 26 comprises three rolling elements 26. Again, the rolling elements 26 of both rows are displaced or offset to one another, for bridging the gap between adjacent second rolling elements 26 to always provide the capability of rolling the bidirectional wheel 18 in the second direction 22.

With regard to FIG. 2c, a motor assisted movement assembly 19, comprising exemplaryly three bidirectional wheels 18 is depicted. Using at least three bidirectional wheels 18 allows to securely position and move the motor assisted movement assembly 19 on a surface.

However, an arbitrary number of bidirectional wheels like one, two, four, five, six, seven, eight or even more bidirectional wheels 18 may be conceivable, possibly with the addition of at least one or two support wheels. Each bidirectional wheel 18a,b,c of the motor assisted movement assembly 19 is adapted to be turned about its individual axis 28 for movement of the respective bidirectional wheel 18a,b,c its individual first direction 20a,b,c.

On the outer circumference of the bidirectional wheels 18a,b,c with regard to the rotational axis 28, a plurality of second rolling elements 26 are arranged. The second rolling elements 26 allow the motor assisted movement assembly 19 to be moved in a direction 22, being a distinct direction for each bidirectional wheel 18, with the second direction 22 being parallel to the axis 28 in the exemplary embodiment of FIG. 2c.

Figure 3:
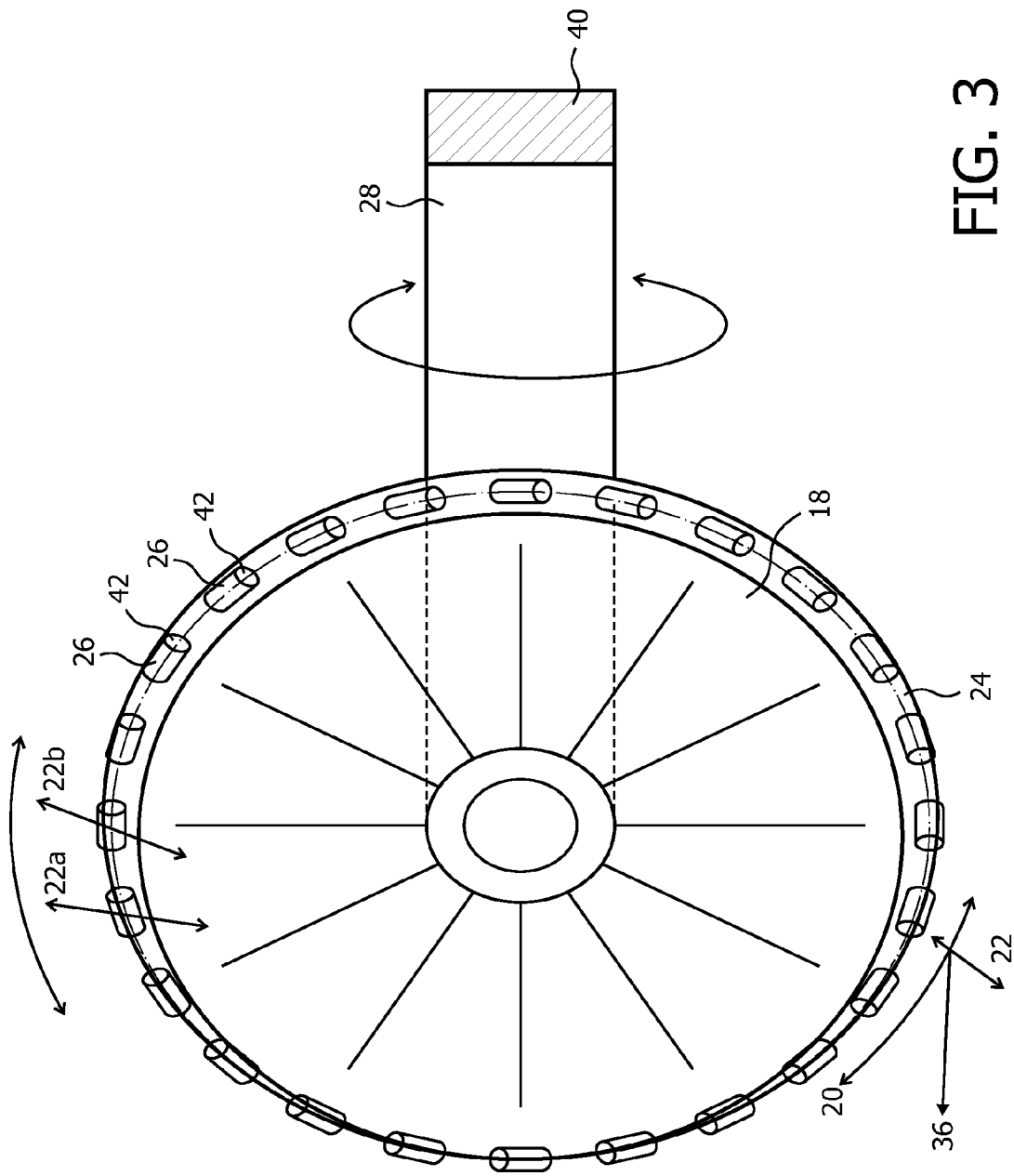
FIG. 3 a detailed schematic of an exemplary embodiment of a bidirectional wheel according to the present invention.

Now referring to FIG. 3, a detailed schematic of an exemplary embodiment of a bidirectional wheel according to the present invention is depicted.

A first motor element 40 is situated at the rotational axis 28 of the bidirectional wheel 18 for moving the bidirectional wheel 18 in the first direction 20, substantially rolling the bidirectional wheel 18 on its outer circumference. The outer circumference and the second rolling elements 26 may be considered to constitute the first rolling element 24 respectively.

On the outer circumference of the bidirectional wheel 18 with regard to axis 28, a plurality of second rolling elements 26 are arranged. In FIG. 3, only one row of second rolling elements 26 is depicted, with the second rolling elements 26 possibly situated such that a movement in the second direction 22 is possible in every conceivable angular position of the bidirectional wheel with regard to the outer circumference/axis 28, due to a tight spacing and possibly small dimensions of the second rolling elements 26.

However, a further row of second rolling elements 26, similar to FIG. 2a or 2b, is conceivable.

Each second rolling element 26 may be movable such that a movement in the second direction 22 may be performed. The movement, thus the rolling of the second rolling element 26 to provide movement in the second direction 22 may be a passive movement, e.g. due to pushing the bidirectional wheel 18 at least partly in the second direction 22 or may be an active movement by employing second motor elements 42, associated with at least a subgroup of second rolling elements 26 for actuation of the second rolling elements 26 for movement in the second direction 22.

So while the bidirectional wheel 18 is moving in the first direction 20 by rolling on the outer circumference of the bidirectional wheel 18, a displacement by employing the second rolling elements 26 in the direction 22 may result in a vector added movement 36 being composed of both the movement in the first direction 20 and the movement in the second direction 22, thus resulting in a vector added movement 36.

Now referring to FIGS. 4a to 4d, different moving scenarios of motor assisted movement assemblies comprising bidirectional wheels according to the present invention is depicted.

Figure 4A:
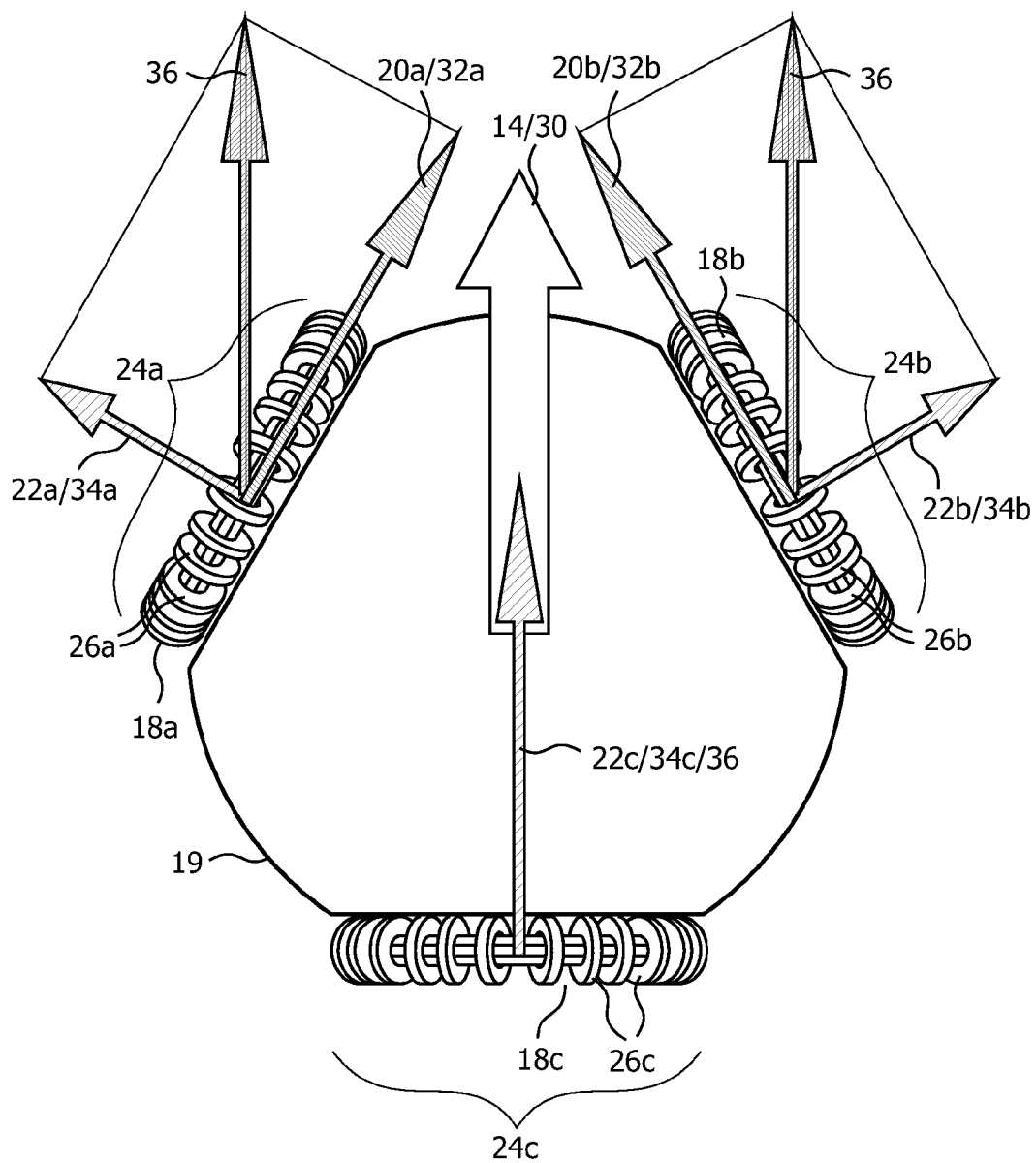

In FIG. 4a, a motor assisted movement assembly 19 comprising three bidirectional wheels 18a,b,c is to be moved in the desired movement direction 14. With regard to bidirectional wheel 18a, the principle of vector addition for obtaining a resulting movement 30/36 is depicted. Bidirectional wheel 18a is moving in a first direction 20 by using the first rolling element 24a, which results in a movement 32a of the first rolling element 24a.

Bidirectional wheel 18b is exemplary performing a similar movement with regard to its first direction 20b since both bidirectional wheels 18a,b, with regard to the first direction 20a,b, are not aligned in parallel. A resulting movement of the bidirectional wheels 18a,b solely in the direction 20a,b would result in some sort of outward slippage of the bidirectional wheels 18a,b. The outward slippage may be seen as being compensated by the movement of the bidirectional wheels 18a,b, in particular the second rolling elements 26a,b, in the second direction 22a,b.

Thus, a resulting vector added movement 36 of a bidirectional wheel 18 is obtainable, which is parallel to the desired movement direction 14, thus resulting in the movement 30 of the motor assisted movement assembly 19.

In FIG. 4a, the third bidirectional wheel 18c is only required to move in its second direction 22c, since the desired movement direction 14 is in this case perpendicular to the first direction 20.

With regard to FIG. 4b, the turning of the motor assisted movement assembly substantially in place about turning points 38 is depicted. The desired movement 14 is thus a circular movement which results in turning the motor assisted movement assembly 19 about the turning point 38. This movement 30 may be obtainable may substantially only moving the bidirectional wheels 18a,b,c in the first direction 20a,b,c for turning.

With regard to FIG. 4c, a linear sideways movement substantially in the first direction 20a of bidirectional wheel 18a is to be obtained. Accordingly, the vector added movement 36b,c of bidirectional wheels 18b,c has to be such that a resulting movement 30 in the direction of the desired movement 14 may be obtained. Again, with regard to bidirectional wheels 18b,c, a resulting vector added movement 36 composed by a movement in a first direction 20b,c and a second direction 22b,c has to be employed for obtaining the resulting movement 30.

With regard to FIG. 4d a turn about the turning point 38 is to be realized. Since turning point 38 in FIG. 4d is not within the center of the motor assisted movement assembly 19 substantially all three bidirectional wheels 18a,b,c have to employ a movement in a first direction 20a,b,c and in a second direction 22a,b,c for obtaining a resulting movement 30 as the desired movement 14.

Now referring to FIG. 5, a schematic of an exemplary embodiment of the motion control element of a motor assisted movement assembly according to the present invention is depicted.

The motor arrangement 40/42 may e.g. be a brushless AC, vector controlled motor arrangement 40/42 for the actuation of the C-arc X-ray system 2, in particular a wheel 9, e.g. a bidirectional wheel 18. A brushless AC (BLAC) motor may in particular employ an electronically-sinusoidal vector controlled commutation system. An according type of motor may provide for a continuous four-quadrant torque and speed range starting from zero.

The motor arrangement 40/42 receives an actuating power via amplifier $K_t$ and provides a feedback regarding its position by an absolute position feedback encoder for commutation and servo control. In FIG. 5, two basic modes may be set, described as mode A, the PID or position mode, and the mode B, the torque/current mode. The servo controller provides functions like brushless AC commutation control, torque/current control loop, position (PID) control loop and "on the fly" control loop switching mechanism.

The Amplifier may provide the electronic commutation and the current loop. Due the motor torque possibly being proportional (Kt) with the current, a torque control may be achieved. The PID control may react on the position error to minimize it. To achieve this, the PID controller may deliver a proportional, the integral and the derivative values from the error signal. The "on the fly" mode switching may ensure that during the transition no can may be felt. This may be achieved by increasing or decreasing the three PID parameters smoothly.

The control principle is depicted by the block diagram shown in FIG. 5, which provides an overview of all the functions of the motor controller. The functions are located in a servo controller and in the control element. The amplifier provides the commutation and the control loop. A current set point is generated by the PID controllers and the feed forward offset. A motor position feedback may be provided by a high resolution absolute encoder.

In case a feed forward controlled system is provided, the set current may be determined by the feed forward algorithm, in particular depending on the position, velocity and acceleration setpoints and the mass, damping, friction and the unbalance parameters. In this case, the set current may in particular equal the offset current. The PID controller may correct deviations of the feed forward model.

In the PID mode or the position or speed control mode, switches in the "act/set input switch" element and "on/off PID" in the servo controller are set to "mode A". The feed forward algorithm may calculate or determine an expected motor current, based e.g. on a physical movement model. The model may contain parameters like friction, damping, mass and unbalance and may refer to the respective physical formula. If the modeling matches, in particular substantially fully matches the modeled real system, a contribution from the PID controller to the current set point to the amplifier may not be required. In this, theoretical case, the movement of the X-ray system 2 may follow a requested or desired trajectory without the support of the PID controller. An according model may also be used as a reference for the assist settings of the assist mode.

During the assist mode, the PID control is switched off and the movement set points are substituted by actual set points from the differenator filter, as opposed to the PID mode where the respective values are provided by the set point generator. In the assist mode, the feed forward mechanism may stay active, but the amount may be reduced to a required assist level. In the assist mode, the unbalance feed forward may be added completely. A damping contribution may be employed to avoid too high a manual speed by e.g. providing a counteracting force, which may result in substantially reducing the mechanical motor output or assisted movement or even counteracting or even opposition, in which case Pd may be even below zero.

With perception parameters or factors $P_m$, $P_d$ and $P_f$, the required or desired assistance may be adjusted. In assist mode, these parameters may be between 0 and smaller than 1, while in PID mode the parameters may be equal to 1. The allowable range of the factors is between 0 and 1 with both margins included.

The actual speed and acceleration is acquired by differentiation and filtering of the actual position feedback, which is performed in the differenator filter. A movement may in particular be activated when the motion controller detects a position deplacement.

Also, preferred positioning may be implemented. By using the assist mode, stopping in pre-programmed positions may be implemented. A user provides a manual indication of a desired direction of movement, in which direction a programmed position may be situated. Near this position, the control may be automatically overruled by the PID position controller to force a smooth and precise stop and the pre-programmed position. The user mode controller provides a smooth control mode switching from current loop to PID loop. After the movement is stopped, the assist mode may again be available.

Furthermore, a break mode may be implemented, which substantially equals a stop at a preferred position, like described earlier. Also, a hold/break function may be realized by keeping a position in PID mode with the motor only being activated when the break position is left.

Figure 6:
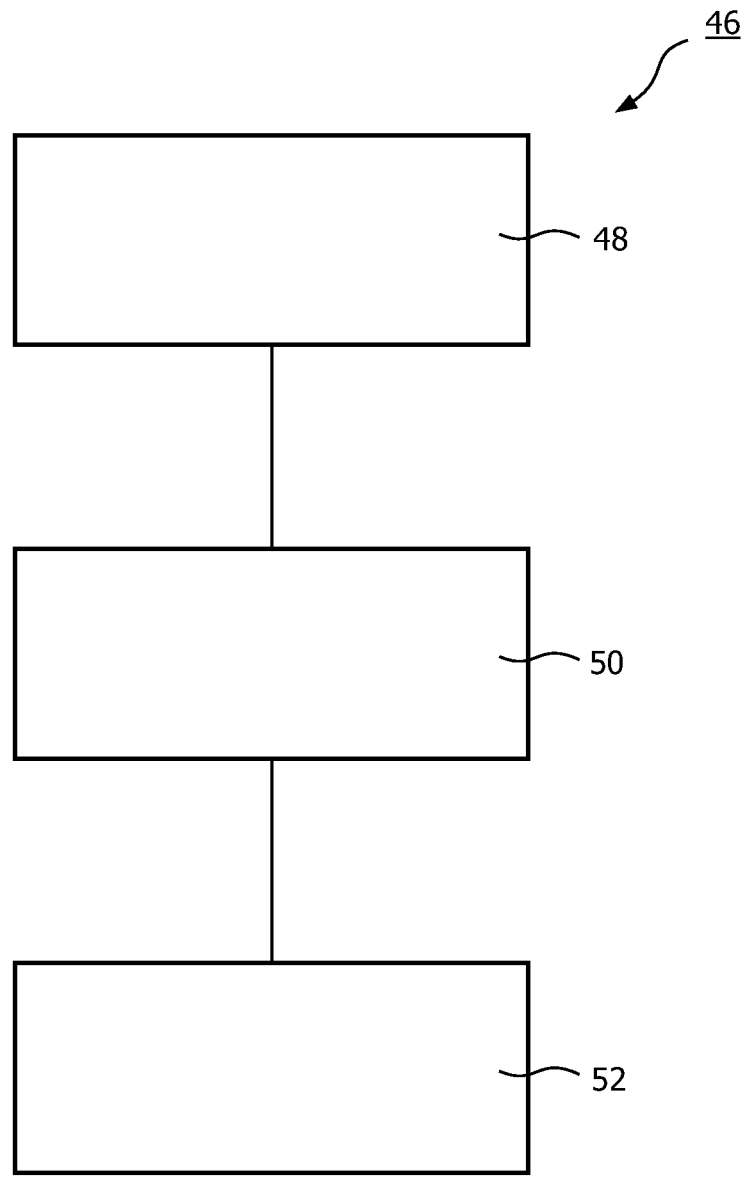
FIG. 6 an exemplary embodiment of the method for motor assisted positioning according to the present invention.

Now referring to FIG. 6, an exemplary embodiment of the method for motor assisted positioning according to the present invention is depicted.

A Method of motor assisted movement 46 is provided, comprising the steps of applying 48 an external force to the motor assisted movement assembly as a manual indication of a desired movement of a motor assisted movement assembly relative to a surface, detecting 50 the external force in a motor assembly or a motor element and assisting 52 the desired movement.

It should be noted that the term "comprising" does not exclude other elements or steps and that "a" or "an" does not exclude a plurality. Also, elements described in association with different embodiments may be combined.

It should also be noted, that reference numerals in the claims shall not be construed as limiting the scope of the claims.

REFERENCE NUMERALS

2 X-ray system
4 X-ray generator
6 X-ray detector
7 X-radiation
8 Wheel arrangement
9 Wheels
10 Object
12 Operator
14 Desired movement direction
15 Handle
16 Indication of desired movement
18a,b,c Bidirectional wheel
19 Motor assisted movement assembly
20a,b,c First direction
22a,b,c Second direction
24 First rolling element
26 Second rolling element
28 Axis
30 Movement of motor assisted movement assembly/resulting movement
32 Movement of first rolling element
34 Movement of second rolling element
36 Vector added movement of wheel
38 Turning point
40 First motor element
42 Second motor element
44 Motion control system
46 Method of motor assisted movement
48 STEP: apply an external force to a motor assisted movement assembly
50 STEP: detect external force in a motor assembly or a motor element
52 STEP: assist desired movement

The invention claimed is:

1. A motor assisted movement assembly configured for, on a surface, moving in response to an external force applied to said assembly, said assembly comprising:
   a bidirectional wheel; and
   a motor arrangement associated with said wheel;
   the motor assisted movement assembly being further configured for, via said wheel, the moving on said surface, said wheel being configured for, without need for pivoting said wheel as to rolling direction on said surface, rolling on said surface in a first direction and on said surface in a second direction different from and non-opposite to said first direction; and, communicatively connected to said wheel, a control element configured for the responding, said responding including detecting application of said external force and assisting movement of said assembly, said assisting comprising applying, via said motor arrangement, additional force in at least one of said first and said second directions so as to at least partly decrease at least one of perceived moving resistance, and perceived moving force, of said assembly.

2. The motor assisted movement assembly of claim 1, said wheel comprising a first rolling element and a second rolling element, said first rolling element being configured for rolling in said first direction, said second rolling element being configured for rolling in said second direction.

3. The motor assisted movement assembly of claim 2, said arrangement comprising a first motor element associated with said wheel by virtue of being associated with said first rolling element, said first motor element being configured for moving said assembly in said first direction.

4. The motor assisted movement assembly of claim 3, said arrangement further comprising a second motor element associated with the said wheel by virtue of being associated with said second rolling element, said second motor element being configured for moving said assembly in said second direction.

5. The motor assisted movement assembly of claim 4, further comprising a sensor and configured for, via said sensor, detecting a torque acting on at least one of the motor arrangement, the first motor element, and the second motor element.

6. The motor assisted movement assembly of claim 1, said external force causing movement of said assembly, as a whole, relative to said surface.

7. The motor assisted movement assembly of claim 1, said assembly featuring at least one mode out of the group consisting of a drive mode, a clutch mode, a freewheeling mode, a brake mode, a motor assist mode, a position mode and a motorized mode.

8. The motor assisted movement assembly of claim 1, further comprising a control element and configured for, via said control element, automatic repositioning in or at a previously set or known position to settle at said position.

9. The motor assisted movement assembly of claim 1, further comprising a motion control element for controlling said additional force.

10. The motor assisted movement assembly of claim 1, further including a control element, said motor arrangement being a direct drive motor arrangement having a break mode by which said assembly automatically, via said control element, stops and settles at a predefined position.

11. An X-ray system comprising the assembly of claim 1, said system further comprising an X-ray generating device and an X-ray detector, said X-ray generating device and the X-ray detector being operatively coupled for acquisition of X-ray images of an object to be examined.

12. The assembly of claim 2, said second rolling element being among a row of second rolling elements, said assembly further comprising a row of additional second rolling elements, the two rows being offset against one another to bridge a gap between two adjacent rolling elements of one row via a rolling element of the other row, said second rolling elements of both rows being configured for coming into direct contact with said surface so as to roll on said surface, thereby resulting in said rolling on said surface.

13. The assembly of claim 2, said second rolling element being among a group of second rolling elements included in said assembly, said assembly further comprising multiple second motor elements and being further configured for applying, via said multiple second motor elements for movement in said second direction, motor force to a corresponding plurality of second rolling elements from among said group.

14. The motor assisted movement assembly of claim 1, said surface being a flat surface.

15. The motor assisted moving assembly of claim 1, wherein said control element is configured for said applying in said first direction and further configured for said applying in said second direction.

16. The motor assisted moving assembly of claim 15, wherein said control element is configured for said applying in the first and second directions simultaneously.

17. The motor assisted movement assembly of claim 16, configured such that, if components of force said application exerts on said wheel are in both said first and said second directions, said additional force is applied in both said first and second directions.

18. A motor assisted movement assembly for responding to an external indication of movement for said assembly relative to a surface, said assembly comprising:
 a bidirectional wheel configured for rolling in a first direction and in a second direction, with the first direction and the second direction being non-parallel; and
 a motor arrangement associated with said wheel;
 said assembly being configured for:
  moving on said surface;
  detecting said indication, said detecting comprising detecting an imparting, to said assembly, of an external force of a magnitude sufficient for overcoming friction with said surface so as to thereby cause said rolling on said surface, said detecting of said imparting comprising detecting an externally caused rolling of said wheel; and,
  via said motor arrangement, assisting, in accordance with said indication, said rolling on said surface in at least one of said first direction and said second direction.

19. The assembly of claim 18, said responding comprising applying, by said assembly, in said assisting, additional force in at least one of said first direction and said second direction, said assembly further comprising a motor element for generating said additional force.

20. The assembly of claim 19, said applying additional force being dynamically responsive to said detecting of said imparting so as to additively contribute to said external force so as to thereby afford an increased overall force.

21. The motor assisted movement assembly of claim 18, further comprising:
 a motor element associated with said wheel and configured for providing force for said assisting, said moving entailing said rolling on said surface; and
 a control element, said assisting being performed according to said control element, said control element comprising a sensor for measuring a parameter of electricity flowing in said motor element, said assisting operating based on the measurement.

22. The motor assisted moving assembly of claim 18, configured for said assisting of said rolling in both the first and second directions.

23. The motor assisted moving assembly of claim 22, configured for said assisting in both directions simultaneously.

24. The motor assisted moving assembly of claim 18, wherein said detecting an externally caused rolling of said wheel entails detecting a torque applied to said wheel in at least one of said first direction and said second direction.

25. The motor assisted moving assembly of claim 24, wherein magnitude of the assisting in a given direction varies with the detected torque in said given direction.

26. The motor assisted moving assembly of claim 18, wherein the rolling being assisted is of said bidirectional wheel.

27. The motor assisted moving assembly of claim 18, wherein said bidirectional wheel is configured for said rolling, without pivoting as to rolling direction on said surface, in both the first and second directions.

28. A vehicle comprising:
a bidirectional wheel configured for, without need for pivoting said wheel as to rolling direction on a surface, rolling on said surface in a first direction and on said surface in a second direction different from and non-opposite to said first direction; and
a motor assisted movement assembly configured for applying, in at least one of said first direction and said second direction, power assist to said wheel to supplement a force that is in a direction along said surface, acts on said bidirectional wheel, and originates from a force externally supplied to said vehicle.

29. The vehicle of claim 28, said surface being a flat surface, said wheel including a first rolling element and a second rolling element, wherein one of the rolling elements is configured for, on said surface, rolling, in said first direction along said surface and the other rolling element is configured for, on said surface, rolling in said second direction along said surface, the first and second directions being angled to one another, wherein said rolling elements are angularly disposed with respect to each other for rolling in their respective directions.

30. The vehicle of claim 28, said surface being a flat surface, wherein said wheel is configured for, without pivoting rotation of said wheel as to rolling directionality along said surface, rolling in any arbitrary direction within a plane in which said first and second directions both reside albeit in dependence upon a direction of said force acting on said bidirectional wheel.

31. An X-ray system comprising the vehicle of claim 28, an X-ray generating device, and an X-ray detector, said device and said detector being operatively coupled for acquisition of X-ray images of an object to be examined.

32. The vehicle of claim 28, wherein said assembly is configured for said applying in both said first direction and said second direction.

33. The vehicle of claim 32, wherein said assembly is configured for said applying in both said first direction and said second direction simultaneously.

34. The vehicle of claim 33, wherein directional components of said force acting on said bidirectional wheel in said first direction and said second direction determine whether said applying operates in said first direction, said second direction, or in both said first and second directions.

35. The vehicle of claim 33, wherein directionality of said force acting on said bidirectional wheel determines a magnitude of power assist applied to said wheel in each of said first direction, if at all, and said second direction, if at all.

* * * * *